United States Patent [19]

Zatko

[11] 4,386,518
[45] Jun. 7, 1983

[54] APPARATUS AND METHOD FOR MEASURING LOW CONCENTRATIONS OF HIGH MOLECULAR WEIGHT POLYMERS IN SOLUTION

[75] Inventor: Jalna R. Zatko, North Wales, Pa.

[73] Assignee: The United States of America as represented by the Secretary of the Interior, Washington, D.C.

[21] Appl. No.: 240,060

[22] Filed: Mar. 4, 1981

[51] Int. Cl.³ ............................................. G01N 11/04
[52] U.S. Cl. ......................................................... 73/55
[58] Field of Search ................ 73/55, 56, 438, 861.52, 73/861.69, 54

[56] References Cited

U.S. PATENT DOCUMENTS 3,167,691  1/1965  Halista ................................. 73/54 X
3,327,522  6/1967  Hoyt ...................................... 73/55
3,420,096  1/1969  Hoyt ........................................ 73/54

FOREIGN PATENT DOCUMENTS 847208   6/1952  Fed. Rep. of Germany ... 73/861.52
2622375  1/1977  Fed. Rep. of Germany .......... 73/54

Primary Examiner—E. R. Kazenske
Assistant Examiner—Joseph W. Roskos
Attorney, Agent, or Firm—William S. Brown; Donald A. Gardiner

[57] ABSTRACT

A system for determining the concentration of polymers in solution by measuring a differential pressure across a section of tubing through which the solution flows, where the tubing is bent in a loop. A drag reduction can be computed from the differential pressure value and the concentration may be determined by referring to calibration data which shows the drag reduction for known concentrations of polymers.

4 Claims, 3 Drawing Figures

APPARATUS AND METHOD FOR MEASURING LOW CONCENTRATIONS OF HIGH MOLECULAR WEIGHT POLYMERS IN SOLUTION

BACKGROUND OF THE INVENTION

1. Field of the Invention

This invention relates generally to a concentration measuring system and more particularly to a system for measuring very low concentrations of high molecular weight polymers in solution.

2. Description of the Prior Art

In various situations, it has become important to be able to measure the concentration of high molecular weight polymers in solution. Where these concentrations are very low, such as 1-10 ppm, it has been particularly difficult to obtain quick and easy measurements. There have been no instruments or methods which are capable of quick, accurate, inexpensive and repeatable measurement of such very low concentrations. Furthermore, the devices which are available are sensitive to such variables as the quality of the solvent, with respect to its turbidity.

Methods which have been used to estimate or measure low concentrations of polymers in solution include nephelometric, colorimetric and complexation methods. The analysis which depends on spectrophotometric absorption measurements is subject to several different interferences. The solvent must be of high quality and free from suspended solids. Gravimetric and chromatographic methods suffer from low quality solvents. Further limitations on precipitation techniques include the time necessary and the expense of the reagents. Chromatographic analysis requires a higher concentration of polymer. Many of the methods are only applicable to particular polymers, and only in concentrations above 10 ppm.

One device developed by the United States Navy for measuring a polymer in solution is shown in U.S. Pat. No. 3,924,448. In order to measure a high concentration of polymer in solution, samples of the solution are diluted according to a specific ratio. Incoming water flows along a straight pipe containing a differential pressure gauge. The drop in pressure of the pure water over this length of pipe is measured. A small amount of solution is then added to the pure water to form the very low concentration solution. The solution is then measured by a differential pressure gauge in the same manner in which the pure water was measured above. Using the two pressure differentials, a percent drag reduction may be calculated. This low concentration can then be determined by a comparison with the calibration data relating concentration to percent drag reduction. After calculating the low concentration values, it is possible to compute the original higher concentration values using the dilution ratio figure. The pressure differentials measured in this system utilize a straight piece of pipe for measurement. The utility of this device is limited, however, since it is not possible to greatly vary the flow rate of the system. Further, since the pressure taps for both water and diluted solution are machined into the lines, the distance over which the pressure drop is measured is rigidly fixed. The variability of the system is therefore greatly restricted since neither the flow rate nor the pressure drop distance is adjustable.

Another system developed by the U.S. Navy is described in U.S. Pat. Nos. 3,327,522 and 3,420,096. In the first patent, a device for measuring the percent drag reduction by measuring a pressure differential along a straight piece of pipe is shown. The sample to be measured is driven along the pipe by a constant speed pump. The second patent uses measurements developed in the system disclosed in first patent in order to measure the molecular weight of polymers in solution. Calibration data is accumulated using known polymers and known concentrations. By measuring drag reduction for various concentrations, the polymer molecular weight may be established. The disadvantage of this system is the use of a constant speed pump which limits the range of flow rates available and the fixed distance between pressure tops. Also, the plunger-type sample chamber is not convenient for continuous, on-line processes or rapid repetitive sample measurements. Further, this system does not attempt to utilize the drag reduction information to measure concentrations of polymers.

SUMMARY OF THE INVENTION

Accordingly, one object of this invention is to provide a novel measurement device for determining the concentration of polymers in solution.

Another object of this invention is to provide a concentration measurement device having a variable flow rate.

A further object of this invention is to provide a concentration measurement device having a pressure differential gauge extending on both sides of a flow line which is bent into a loop.

An additional object of this invention is to provide a novel measurement for determining the concentration of polymers in solution.

Briefly, these and other objects of the invention are achieved by providing a variable flow rate pump which receives a solution of unknown concentration and forwards it through a main flow line which contains a snubber for handling surges under pressure, a safety relief valve, and a pressure gauge. A flow line of reduced size is then provided which carries the solution to a differential pressure gauge. The length of flow line between the two sensors of the pressure gauge is bent into a loop. The output of the differential gauge gives an indication of drag reduction, and hence concentration.

BRIEF DESCRIPTION OF THE DRAWINGS

A more complete appreciation of the invention and many of the attendant advantages therof will be readily obtained as the same becomes better understood by reference to the following detailed description when considered in connection with the accompanying drawings, wherein.

DESCRIPTION OF THE PREFERRED EMBODIMENTS

Figure 1:
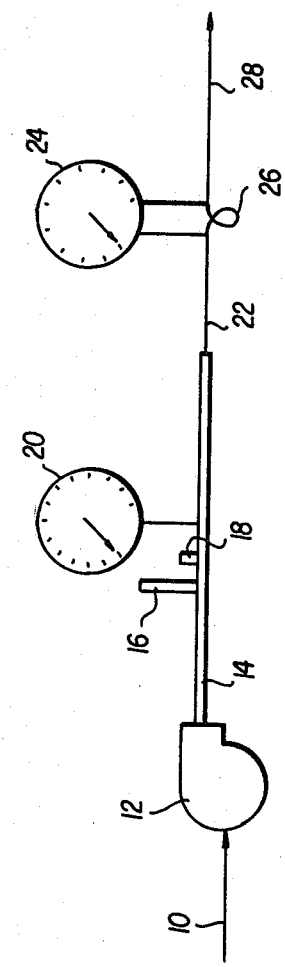
FIG. 1 is a schematic diagram of the components of the invention.

Referring now to the drawings and more particularly to FIG. 1 therof, wherein the overall arrangement of the various functional parts of the measuring apparatus is shown, an input solution containing a low concentration of a high molecular polymer is introduced into a sample inlet, 10. The polymer used may be polyethylene oxide or polyacrylamide, for example, and the solvent may be any material which will dissolve these polymers, such as distilled water. The sample inlet is directly connected to a conventional metering pump 12, which has an adjustable flow rate. The flow rate, for example, can vary from 0–1000 mls per minute. The pump may be a positive displacement rotating and reciprocating piston metering pump, for example. The flow rate may be adjusted to vary the Reynolds number of the flow. The output side of the metering pump is connected to a flow line, 14. A snubber 16 is connected to the line and provides an air column which dampens any pulsations of the solution in the flow line and hence avoids unsteady readings o the pressure gauges. A conventional safety relief valve 18 is also connected to the flow line as a precaution, to avoid a high pressure buildup should the flow line become plugged. A conventional pressure gauge 20 is connected to the flow line to provide a direct reading of the pressure within the flow line. The surfaces of the pump and pressure gauges which come in contact with the test solution are made of 316 stainless steel. Likewise, the flow line and connections are made of similar material.

A reduced flow line 22 is connected to the output end of the flow line 14. The outside diameter of flow line, 14, may be ¼ inch. The outside diameter of the reduced flow line may be ⅛ inch with an inside diameter of 0.09 inch. The reduced flow line initially extends in the same direction as the flow line 14, but is then sharply bent into a loop 26 before returning to a final portion extending in the same direction as the first portion. The initial straight portion of the reduced flow line may be 5 inches in length, while the length of the loop may be 13 inches. The final portion of the reduced flow line leads to an outlet 28, which may be a drain or a collecting vessel for receiving the solution which has been measured. A conventional differential pressure gauge 24 measures the difference in pressure between the solution in the initial portion of the reduced flow line and that of the solution in the final portion of the reduced flow line. The differential pressure gauge may have a 6 inch diameter dial and a scale of 0 to 50 PSID in ¼ PSID graduations.

The portion of the reduced flow line 22 which has been bent into a loop 26 forms a very important feature of the device. In order to obtain accurate results, it is necessary to obtain turbulent flow between the two pressure measureing points. Turbulence is imparted to the liquid as it flows around the loop. Further turbulence is created by the reduction of the flow line diameter and by setting the pump for a high flow rate.

Increased versatility is also obtained by the present design. The length of tubing placed between the pressure taps on the differential pressure gauge may be varied and hence the distance over which the pressure drops are measured can be changed. The combined variability offered by an adjustable pump flow rate and differential measuring distances can cover a wide spectrum of drag-reducing polymer systems.

It is known that long chain, high molecular weight polymers exhibit an unusual viscosity-related behavior in solutions under turbulent flow conditions. In very low concentrations, polymers will decrease the drag or friction of a solvent during turbulent flow. This phenomenon has been termed drag reduction. The effect is directly related to the pressure of the fluid measured over a given length of tubing during turbulent flow. The amount of drag reduction is a function of the type of polymer, its concentration in solution, the solvent, the flow rate of the solution, the Reynolds number, the temperature and the length and tube diameter over which the pressure drop is measured. By keeping all the variables except the polymer concentration fixed, it is possible to establish a calibration curve of percent drag reduction versus polymer concentration. Once this curve is established, it is possible to determine the concentration of the polymer by measuring the percent drag reduction.

Since the percent drag reduction is defined to be:

$$\text{percent drag reduction} = [(\Delta P_s - \Delta P_p)/\Delta P_s]100 \quad (1)$$

where $\Delta P_s$ is the differential pressure reading of the solvent and $\Delta P_p$ is the differential pressure reading of the polymeric solution, it is possible to determine the drag reduction for a specific concentration by merely measuring the differential pressure of that solution and the differential pressure of the solvent alone.

Tables 1 and 2 below show data obtained by this procedure for solutions of polyethylene oxide and polyacrylamide respectively.

| Test Solution | $\Delta P_s$ | $\Delta P_p$ | pct D.R. |
|---|---|---|---|
| Distilled water | 43.50 | — | — |
| Polyethylene oxide in distilled water at: | | | |
| 2 ppm | — | 37.50 | 13.8 |
| 4 ppm | — | 33.75 | 22.4 |
| 6 ppm | — | 32.00 | 26.4 |
| 8 ppm | — | 31.00 | 28.7 |
| 10 ppm | — | 30.75 | 29.3 |
| Distilled water | 43.50 | — | — |
| Anionic polyacrylamide in distilled water at: | | | |
| 2 ppm | — | 39.00 | 10.3 |
| 4 ppm | — | 34.50 | 20.7 |
| 6 ppm | — | 31.00 | 28.7 |
| 8 ppm | — | 30.00 | 31.0 |
| 10 ppm | — | 29.50 | 32.2 |

Figure 2:
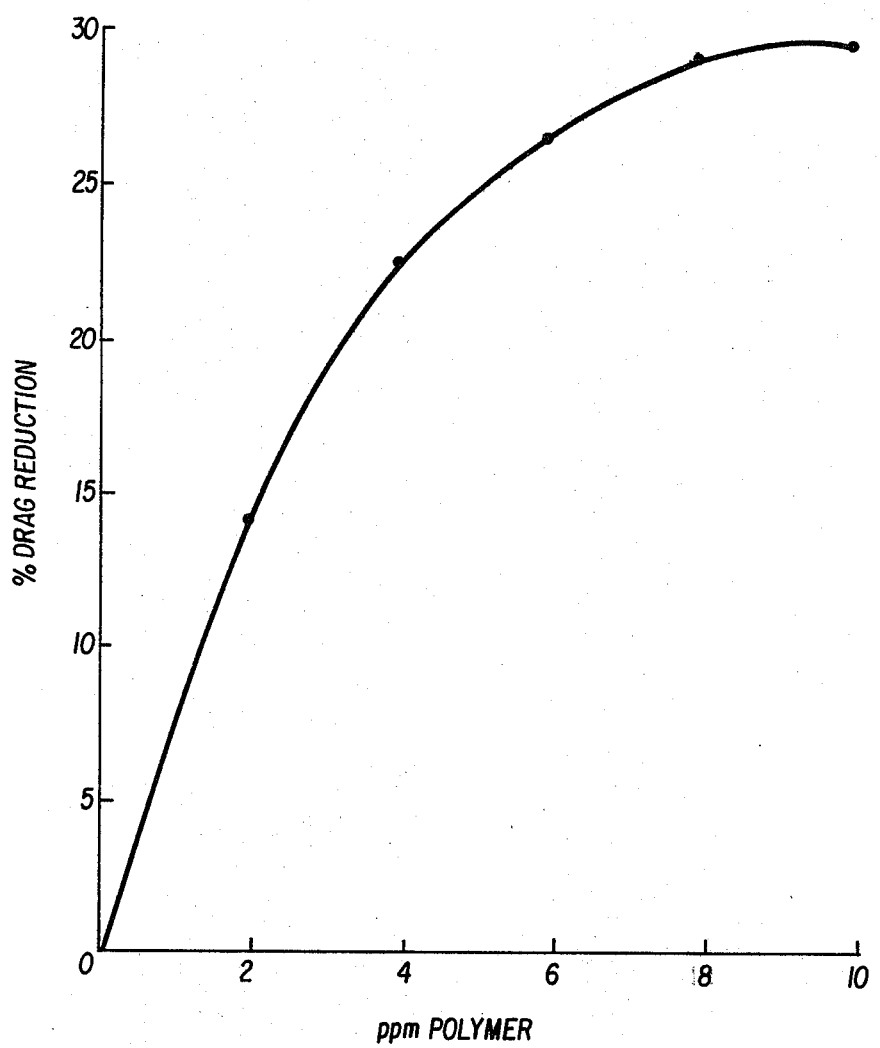
FIGS. 2 and 3 are graphs showing the relation between percent drag reduction and concentration of polymer for two different types of polymers.
Figure 3:
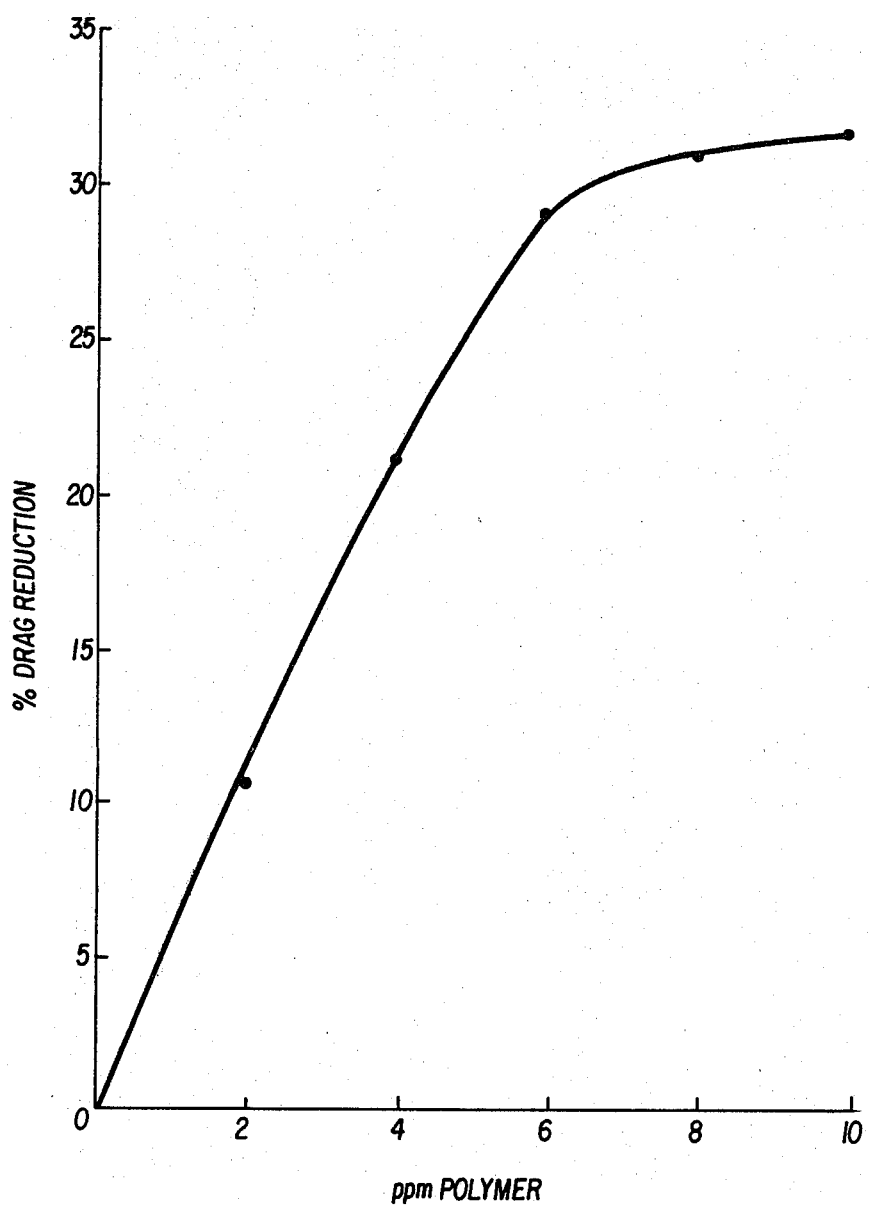

A curve can be established by using the data in the tables to locate a number of drag reduction points. FIGS. 2 and 3 show curves formed by this method. FIG. 2 shows the drag reduction effect for various concentrations of polyethylene oxide in distilled water. FIG. 3 shows the drag reduction effect for various concentrations of a polyacrylimide in distilled water. The vertical axis of each figure represents percent drag reduction while the horizontal axis represents concentrations of polymers in solution. The units of the horizontal axis are parts of polymer per million parts of solution. The vertical axis is measured as a percentage and hence is unitless. Once such a curve has been established, it is possible to measure the concentration of such a polymer by utilizing the apparatus shown in FIG. 1. After the differential pressure of the solution and solvent have been measured, the percent drag reduction may be calculated and the proper concentration may be located on the drag reduction effect curve.

In operation, the user first establishes calibration data and curves as explained in the paragraph above. The user then takes a solution of unknown concentration and places it into the sample inlet, 10, of the device. The variable flow pump forces the liquid at a specified rate through the flow line 14, and into the reduced flow line 22. The solution proceeds around the loop in the reduced flow line causing much turbulence. The differential pressure gauge, 24, perceives the difference in pressure in the reduced flow line on either side of the loop. The user may then use this differential pressure measurement to determine the concentration. The percent drag reduction is first calculated using the equation cited above. This value of drag reduction is compared to known data on the calibration curve and hence the concentration is determined.

The apparatus described is simple to construct and operate. It is not sensitive to factors which create problems in other measuring instruments, such as solvent quality and solvent turbidity. The sample inlet provides a convenient arrangement for incorporating concentration measurements in a continuous, on-line process. Since the dimensions of the device are only about 3 feet long by 1½ feet wide, this apparatus can be used as a portable measuring device. The measurements are rapid and no special reagents or analysis techniques are required. Very low concentrations of polymer, such as 1-10 ppm, may be measured. The tubing sizes and other apparatus are commercially available and require no special machining. Hence, the apparatus is simple, easy to use and very accurate.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Apparatus for measuring low concentrations of high molecular weight polymers in solution comprising:
   sample inlet means for receiving a polymeric solution of unknown concentration;
   an adjustable flow rate metering pump connected to said sample inlet means for controlling the flow rate of the sample;
   main flow line means for receiving the discharge of said pump;
   reduced flow line means having smaller diameter than that of said main flow line means and having an input end connected to the output end of said main flow line means;
   said reduced flow line means being straight at each end and having a single loop in the center region thereof, whereby turbulence of flow of the sample is increased;
   differential pressure gauge means having two measuring points, each point being connected across said loop to a differential straight portion of the reduced flow line for producing an indication of the difference in pressure of the reduced flow line means at the two measuring points;
   whereby the indication of the differential pressure gauge means is indicative of the percentage drag reduction of the solution and the concentration of the polymer in solution.

2. The measuring appartus of claim 1, further comprising:
   pressure gauge means for determining line pressure, snubber means for dampening pulsations and pressure relief valve means for preventing high pressure build up connected to the main flow line means.

3. The measuring apparatus of claim 1 wherein the length of said loop may be varied.

4. A method of measuring low concentrations of high molecular weight polymers in solution comprising the steps of:
   pumping a sample of the solution, by means of an adjustable flow rate metering pump, through a main flow line and a reduced flow line having a single loop in the center region thereof, whereby turbulence of flow of the sample is increased;
   measuring a difference in pressure between two points on said reduced flow line, where the reduced flow line between the two points includes said loop;
   determining the drag reduction caused by said polymers from the pressure difference; and
   comparing said drag reduction value to calibration data to determine the polymer concentration.

* * * * *